United States Patent [19]
Carol

[11] Patent Number: 4,827,926
[45] Date of Patent: May 9, 1989

[54] FLEXIBLE SUPPORT ARM FOR MEDICAL INSTRUMENTS

[76] Inventor: Mark P. Carol, 5793 Harborside, Tampa, Fla. 33615

[21] Appl. No.: 68,263

[22] Filed: Jun. 30, 1987

[51] Int. Cl.⁴ .............................................. A61B 19/00
[52] U.S. Cl. .................................. 128/303 R; 604/283
[58] Field of Search .................... 604/283, 280; 128/4, 128/1 R, 303 R, 303 B

[56] References Cited

U.S. PATENT DOCUMENTS

| | | | |
|---|---|---|---|
| 103,023 | 5/1870 | Dalbey | 128/1 R |
| 861,349 | 7/1907 | Beaubien | 128/1 R |
| 3,817,249 | 6/1974 | Nicholson | 128/303 B |
| 4,068,655 | 1/1978 | LeRoy | 128/1 R |
| 4,386,602 | 6/1983 | Sheldon et al. | 128/4 |
| 4,614,187 | 9/1986 | Mulhollan et al. | 128/303 R |
| 4,700,691 | 10/1987 | Tari et al. | 128/1 R |
| 4,705,038 | 11/1987 | Sjostrom et al. | 128/303 R |

Primary Examiner—John D. Yasko
Attorney, Agent, or Firm—Ben D. Tobor

[57] ABSTRACT

A flexible, radiolucent support arm for use with medical instruments in surgical procedures can have its geometric configuration and orientation readily altered by the surgeon, and the support arm for a medical instrument, such as a brain retractor blade, can also be used to provide application of a fluid suctioning force to the operative site.

16 Claims, 2 Drawing Sheets

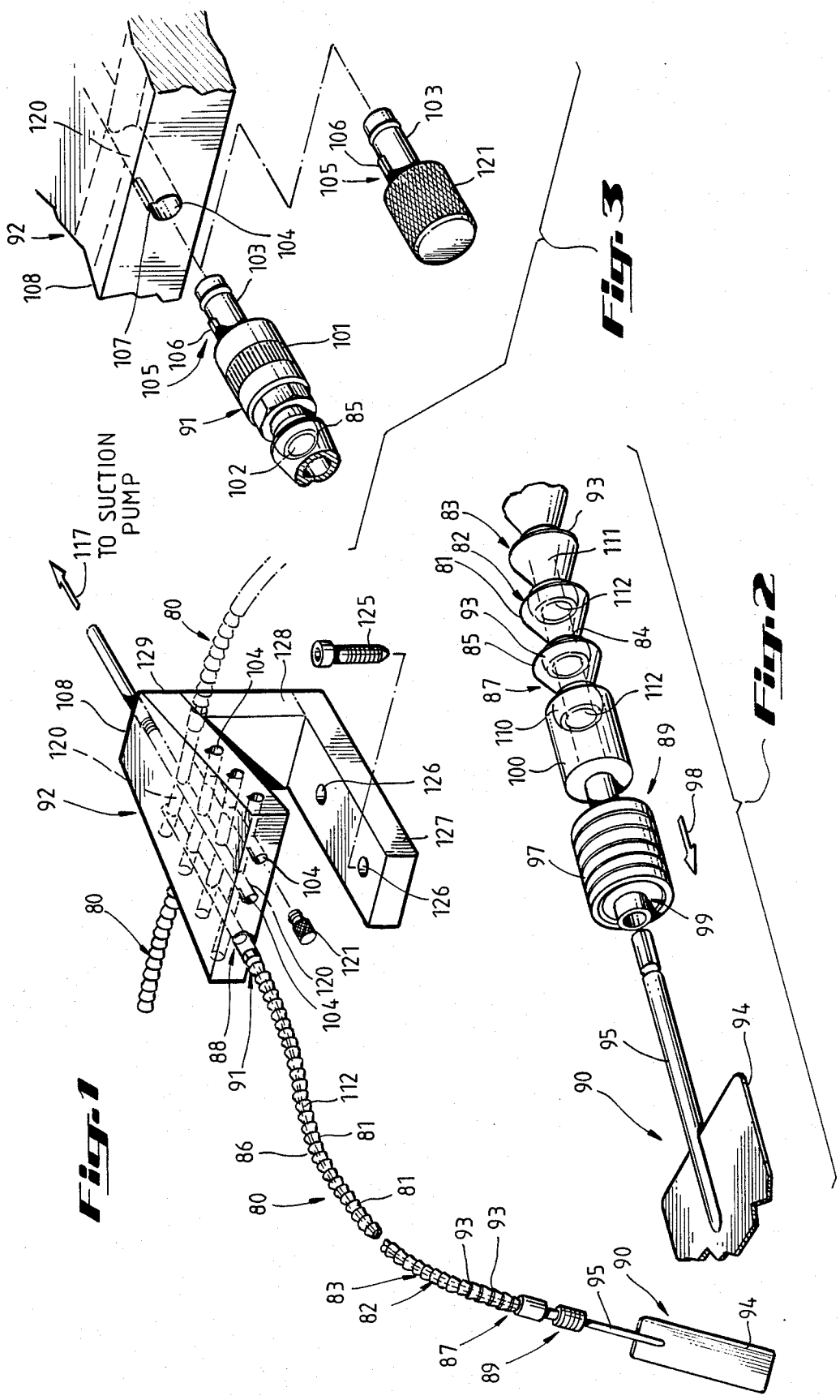

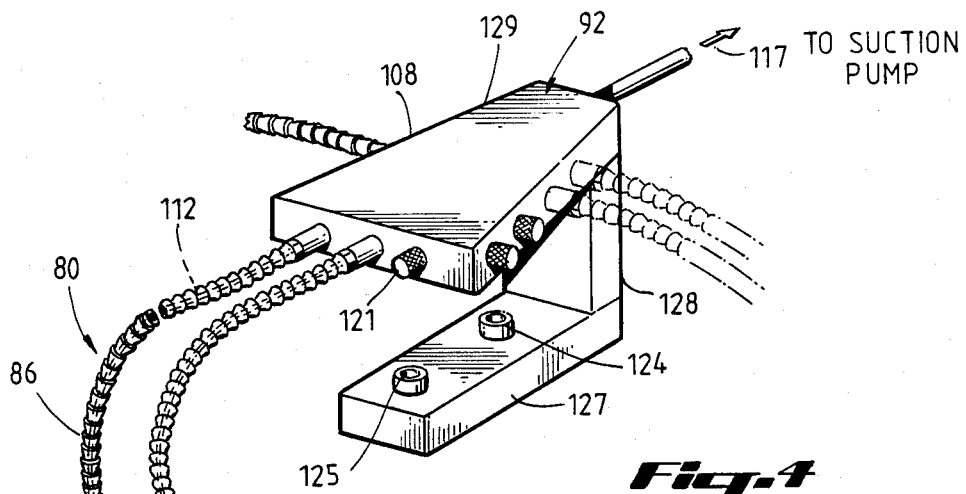
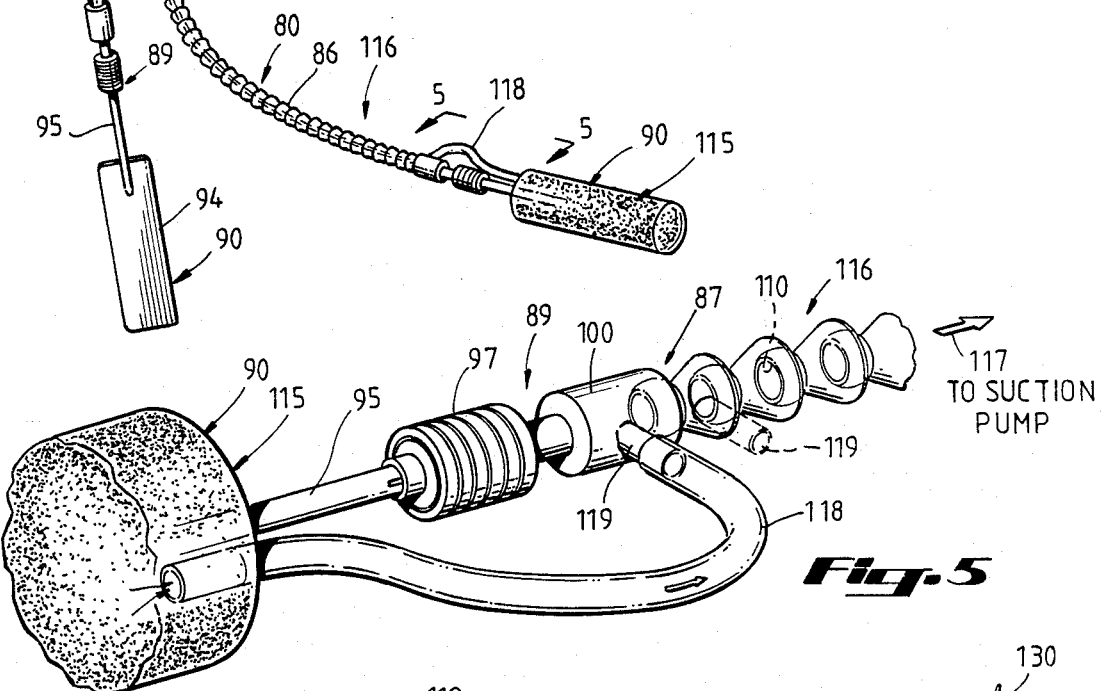
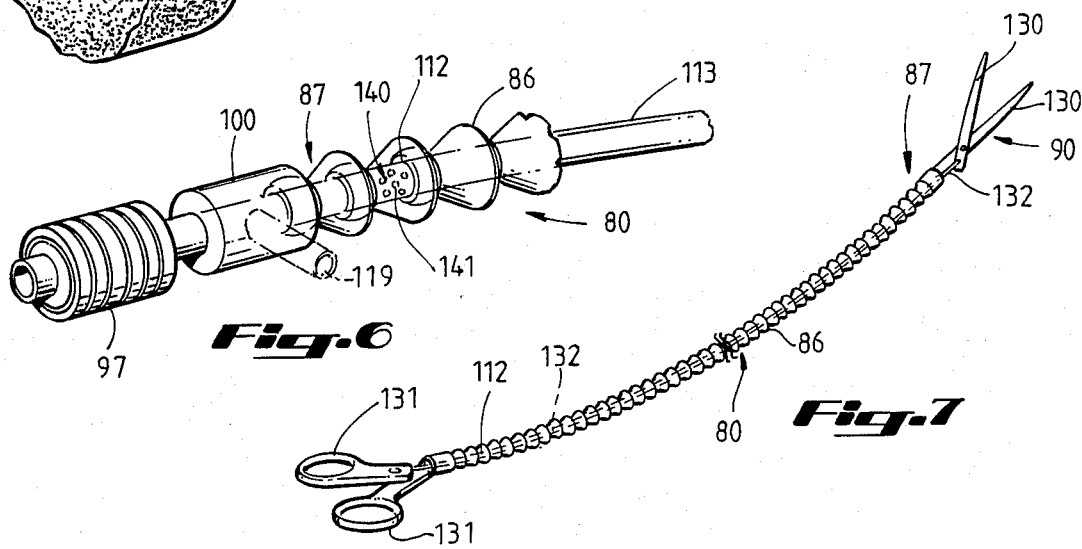

FLEXIBLE SUPPORT ARM FOR MEDICAL INSTRUMENTS

FIELD OF THE INVENTION

The invention relates to a flexible support arm for medical instruments for use in surgical procedures, particularly for supporting a brain retractor in neurosurgery.

DESCRIPTION OF THE PRIOR ART

The practice of neurosurgery typically requires the use of a system for holding back, or retracting, the brain so as to gain access to the area on which the surgery is being performed. Prior to the development of delicate microscope neurosurgery procedures, portions of the brain could be retracted by use of a flat blade, or spatula-type, device which was held by a surgical assistant while the surgeon operated on the area in question. With the advent of delicate microscope neurosurgery procedures, it became necessary to provide continual retraction of the brain; however, such delicate microscope procedures require less movement of the brain than is possible from an assistant manually holding a flat blade retractor against the brain. Accordingly, various types of self-retaining brain retractors were developed.

One type of self-retaining brain retractor includes a blade type brain retractor mounted on a rod, which rod is associated with a number of other rods and a plurality of swivel joints. By adjusting the lengths of the various rods and the angular disposition of the swivel joints, and locking them with respect to each other, the desired disposition of the brain retractor blade can be obtained. The rods could be secured to the patient's skull by means of cerebellar retractor, which includes self-retaining sharp prongs, which hold the muscles back, and the rods are attached to the cerebellar retractor. Alternatively, a rod could be directly secured to the skull, as by drilling a hole in the skull and one of the rods could be screwed into the hole; or one of the rods could be received by a clamp which clamps to the skull at the site of the brain surgery, and the rod could be attached to the clamp.

A disadvantage associated with all of the previously described self-retaining brain retractors is that all of these rod-type, self-retaining brain retractors requires the tightening and loosening of several joints and components in order to change their geometric relationship to change the orientation of the brain retractor blade. These manual operations can be time consuming.

Another type of brain retractor support arm has been developed which includes a plurality of metallic pieces held together by a metal cable passing through each piece, to thus form a flexible chain. Upon obtaining the desired geometric relationship of the flexible arm, the cable is tightened to lock the individual components into the desired geometric relationship. Although this type of flexible arm for brain retractors does eliminate the numerous tightening and adjusting steps previously necessary, it is still necessary to tighten the cable so as to put a compressive force upon all the pieces which form the flexible chain to maintain the desired geometric relationship. Furthermore, during delicate surgery, the need for the surgeon to loosen and tighten the cable to modify the geometric relationship of the brain retractor blade with respect to the patient can make it more difficult for the surgeon to maintain his attention to area being operated upon; or alternatively may require the presence of a surgical assistant to move the brain retractor blade, as by loosening and tightening the cable. Sometimes, such an assistant may, or may not, be skilled in the art of the necessary adjustment of the location of the brain's retractor blade.

Another disadvantage with respect to all of the prior art apparatus for supporting a brain retractor blade is that all of those devices are metallic structures, and therefore are not radiolucent. Radiolucency of equipment used in neurosurgery is becoming very desirable, in that such radiolucency allows X-rays to be taken in the operating room of the operative surgical site to give the surgeon more directional guidance than he might have from just a visual inspection alone.

During many surgical procedures, suctioning of the operative site is necessary in order to keep the operative site free from blood and other fluids which may obscure the surgeon's visualization of the site in question. With all the prior art support devices for brain retractor blades, suction needs to be provided by a separate hose and suction system, which causes an additional object at the operative site which can potentially obstruct the surgeon's field of vision.

In other types of surgical procedures performed upon the human body, various types of medical instruments are utilized; however, such instruments have a fairly standardized construction, and a limited range of shapes and sizes associated with such instruments. The human body, on the other hand, comes in all shapes and sizes, whereby it would be desirable to be able to alter the geometric relationship of a particular medical instrument. Some surgical instruments have been made of materials which can be bent or molded to the surgeon's particular needs, as by manufacturing some small medical instruments from thin-walled metal materials to provide pliability. A disadvantage of such instruments is that repeated bending of the instrument can cause the shearing of the medical instrument into two pieces, thus shortening the useful life of the medical instrument. Additionally, such medical instruments, after being bent once into a desired shape, are extremely difficult to restore the instruments to their original shape, or perhaps other desired shapes. Additionally, such bendable medical instruments have not been made for instruments of an active nature, such as needle holders, scissors, and clip appliers.

Accordingly, prior to the development of the present invention, there has been no flexible support arm for medical instruments for use in surgical procedures which is: radiolucent; easily altered into a different geometric configurations and orientations without an excessive number of manual steps to obtain the required orientation; easily altered by the surgeon without the necessity of a surgical assistant; able to be used to perform other functions, such as provide suctioning of undesired fluids from the operative site; and able to be utilized with active medical instruments, such as scissors. Therefore, the art has sought a flexible, support arm for use in surgical procedures which is: radiolucent; easily altered and modified into different geometric configurations and orientations without an excessive member of manual steps; easily altered by the surgeon, and does not require a surgical assistant; able to allow other functions to be performed at the operative site such as suctioning away undesired fluids from the operative site; and able to be utilized with active medical instruments, such as scissors.

SUMMARY OF THE INVENTION

In accordance with the invention, the foregoing advantages have been achieved through the present flexible, radiolucent support arm for medical instruments for use in surgical procedures. The present invention includes: a plurality of plastic connectors, each connector having a first and second end, a ball member being disposed on the first end, and a socket member being disposed on the second end; the ball member of each connector being frictionally received within the socket member of an adjacent connector and retained in a desired geometric relationship with respect to the adjacent connector until a force sufficient to overcome the frictional force between the mating ball and socket member is applied to alter the orientation between adjacent connectors; the plurality of connectors being associated with each other to form an elongate, flexible member having first and second ends; means for retaining a medical instrument disposed at the first end of the elongate, flexible member; and means for attaching the elongate, flexible member to a support member, the attachment means being disposed at the second end of the elongate flexible member, whereby upon application of a force to at least some of the connectors, sufficient to overcome the frictional force between adjacent connectors, the orientation of the first end of the elongate, flexible member with respect to the second end of the elongate, flexible member may be altered into a second orientation, which automatically remains until another force is applied to the elongate flexible member.

A feature of the present invention is that the medical instrument may be a brain retractor blade and the support member may be a skull clamp. A further feature feature of the present invention is that the medical instrument may have associated therewith a fluid absorbent material and the elongate, flexible member includes means for applying a fluid suction force to the fluid absorbent material. An additional feature of the present invention is that the fluid suction force application means may include a fluid passageway extending through the elongate, flexible member in fluid communication with the fluid absorbent material, and adapted to be associated with the suction pump.

Another feature of the present invention is that the medical instrument may be a pair of scissor blades, and the support member may be a pair of scissor handles. An additional feature of the present invention is that a passageway may extend between the first and second ends of each connector, and each ball member is received within an adjacent socket member in a fluid and gas tight relationship, whereby a fluid and gas tight passageway extends between the first and second ends of the elongate, flexible member. A further feature of the present invention is that a passageway may extend between the first and second ends of each connector to form a passageway extending between the first and second ends of the elongate, flexible member, and a fluid and gas tight, flexible conduit member may be disposed within the passageway extending between the first and second ends of the flexible elongate member.

Another feature of the present invention is that a passageway may extend between the first and second ends of the flexible, elongate member, and an electrical wire may extend therethrough in an electricity transmitting relationship between an electrical, medical instrument, adapted to be retained by the retaining means, and the support member. Another feature of the present invention is that a passageway may extend between the first and second ends of the flexible, elongate member, and the passageway is at least partially filled with a heat sensitive material which first permits relative movement between adjacent connectors at a first temperature, and upon being heated to a second temperature, subsequently does not permit relative movement between adjacent connectors. The heat sensitive material may be a plurality of polystyrene beads, which after being heated to the second temperature solidify to provide rigidity between adjacent connectors.

The flexible, radiolucent support arm for medical instruments for use in surgical procedures of the present invention, when compared with previously proposed prior art support arms, has the advantages of: being radiolucent; is easily altered without an excessive number of manual steps; is easily altered by the surgeon; can serve other functions at the operative site such as providing suctioning away of undesired fluids; and is able to be used with active medical instruments, such as scissors.

BRIEF DESCRIPTION OF THE DRAWINGS

In the drawings:

FIG. 1 is a perspective view of a flexible, radiolucent support arm for medical instruments for use in surgical procedures in accordance with the present invention;

FIG. 2 is an exploded view of a portion of the arm of FIG. 1;

FIG. 3 is an exploded view of a portion of the arm of FIG. 1;

FIG. 4 is a perspective view of a flexible, support arm in accordance with the present invention illustrating its use to provide suctioning of undesired fluids from the operative site;

FIG. 5 is an exploded view of a portion of the flexible, support arm of FIG. 4;

FIG. 6 is an exploded view of another embodiment of the flexible support arm of FIG. 1 in accordance with the present invention; and FIG. 7 is a plan view of a flexible, support arm in accordance with the present invention when used to provide a surgical scissors.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

In FIGS. 1 and 2, a flexible, radiolucent support arm 80, in accordance with the present invention, is shown to comprise a plurality of plastic connectors 81, each connector 81 having a first and second end 82,83, a ball member 84 being disposed on the first end 82 and a socket member 85 being disposed on the second end 83. The ball member 84 of each connector 81 is frictionally received within the socket member 85 of an adjacent connector 81, as will be hereinafter described in greater detail. The plurality of connectors 81 are associated with each other to form an elongate, flexible member 86 having first and second ends 87, 88. A means for retaining 89 a medical instrument 90 may be disposed at the first end 87 of the elongate, flexible member 86. At the second end 88 of the elongate, flexible member 86, may be disposed a means for attaching 91 the elongate, flexible member 86 to a support member 92. As will be hereinafter described in greater detail, upon application of a force to the flexible elongate member 86, via at least some of the connectors 81, the orientation of the first end 87 of the elongate flexible member 86 with respect to the second end 88 of the elongate flexible member 86 may be altered into a second orientation which automatically remains until another force is applied to the support arm 80 by the surgeon.

As illustrated in FIG. 2, the ball members 84 of each connector 81 are frictionally and tightly, received within the socket member 85 of adjacent connectors 81, whereby each connector 81 is maintained, and retained in a desired geometric relationship with respect to each other by the frictional retaining force. As seen in FIGS. 1 and 2, each socket member 85 includes an annular lip surface 93 which retains each ball member 84 within socket member 85. Connectors 81, retaining means 89 and attachment means 91 are all preferably made of a plastic material, whereby the flexible, support arm 80 will be radiolucent and not appear in X-rays. Any suitable plastic materials could be used, provided it is has the requisite characteristics to withstand the necessary sterilization temperatures encountered in an operating room, and to withstand the frictional forces exerted by the movement between adjacent ball and socket members 84, 85 of connectors 81 without cracking or being damaged.

Still with reference to FIGS. 1 and 2, the medical instrument 90 used in conjunction with flexible, support arm 80 may be a conventional brain retractor blade 94 mounted upon a stainless steel rod 95 in a conventional manner. Blade rod 95 has an end 96 which may be received within retainer means 89 of flexible-support arm 80 in a conventional manner. For example, retainer means 89 may include an outer cylindrical member 97 which is spring biased in the position shown in FIG. 2. Upon application of a longitudinal force in the direction of arrow 98, an internal gripping means 99 is opened to permit the insertion of blade end 96 into gripping means 99. Upon release of cylindrical member 97, it springs back into the position shown in FIG. 2 and the internal gripping means 99 locks upon blade end 96, in a conventional manner. Retainer means 89 may be provided with a retainer socket member 100 which frictionally receives ball member 84 of the connector 81 disposed at the first end 87 of the elongate, flexible member 86 as seen in FIG. 2.

With reference to FIGS. 1 and 2, attachment means 91 may comprise a cylindrical attachment member 101 having a ball member 102 disposed thereon which mates with the socket member 85 of the connector 81 disposed at the second end 88 of the elongate, flexible member 86. Attachment member 101 may include a plug 103 which is matingly received within support member 92 as will be hereinafter described in greater detail. Support member 92 is preferably provided with an opening 104 which receives the attachment means 91 plug member 103, attachment plug 103 being preferably provided with an alignment means 105, which may be a key or plug 106 which is matingly received by a corresponding keyway or opening 107 and opening 104 formed in support member 92. Support member 92 of FIGS. 1 and 2 comprises a skull clamp 108 as will hereinafter be described in greater detail.

With reference to FIGS. 2 and 5, it is seen that the upper portion 110 of each ball member 84 disposed on the first end 82 of connector 81 has been removed, whereby a passageway 111 is formed to extend between the first and second ends 82, 83 of each connector 81. After the plurality of connectors 81 have been formed into the elongate, flexible member 86, as previously described, a passageway 112 (in dotted lines in FIG. 1) is thus formed and extends between the first and second ends 87, 88 of elongate, flexible member 86, the use for which will be hereinafter described in greater detail. If each ball member 84 is received within an adjacent socket member 85 in a fluid and gas tight relationship, passageway 112 will be a fluid and gas tight passageway, the use for which will be hereinafter described in greater detail. By controlling the tolerances of the fit of the ball member 84 within socket member 85, including the tightness, or force exerted by annular lip surfaces 93 of socket member 85 upon ball member 84, ball member 84 can be received within socket member 85 in the desired fluid and gas tight relationship. Alternatively, as illustrated in FIG. 6, a fluid and gas tight, flexible conduit member 113 can be disposed through elongate, flexible member 86 within passageway 112 to provide a fluid and gas tight passageway extending between the first and second ends 87, 88 of elongate, flexible member 86. In the embodiment shown in FIG. 6, the mating of ball and socket members 84, 85 is only sufficient to provide the desired frictional force to maintain the desired orientation and geometric relationship of elongate, flexible member 86; however, the tightness of the fit between the ball and socket members 84, 85 may not be sufficiently tight so as to provide a fluid and/or gas tight relationship between the ball and socket members 84, 85 of connectors 81.

With reference to FIGS. 4, 5, and 6, the purpose of passageway 111, 112, and 113 will be described in greater detail. As previously described, it is many times desireable during surgical procedures to remove undesired fluids from the operative site. The support arm 80 of the present invention can be utilized to assist in providing the removal of these undesired fluids, as by suction, without the necessity of another separate suction hose being disposed within and about the operative site. The medical instrument 90 can have associated therewith a fluid absorbent material 115 and passageway 112 can provide a means for applying 116 a fluid suction force to the fluid absorbent material 115, whereby undesired fluids from the operative site can be drawn away from the operative site. As shown in FIG. 4, passageway 112 (shown in dotted lines) forms the desired fluid passageway extending through the elongate, flexible member 86 and it is in fluid communication with the fluid absorbent material 115, and is adapted to be associated with a suction pump, indicated schematically at 117, as will be hereinafter described in greater detail. Fluid absorbent material 115 may be any conventional material utilized to absorb undesired fluids in a surgical environment, such as a fiber free material that absorbs the undesired fluid. The fluid absorbent material 115 can be formed in any desired shape. One brand of fluid absorbent material which has been found useful in practicing the present invention is sold under the band name Merocel ®, manufactured by Americal Corporation. Medical instrument 90 may also comprise a brain retractor blade 94, as previously described, and the brain retractor blade may have a coating of the fluid absorbent material 115 applied thereto.

As seen in FIG. 5, passageway 112 may be disposed in a fluid transmitting relationship with the fluid absorbent material 115 as by use of a tubular member 118 in fluid communication between the fluid absorbent material 115 and the fluid passageway 112 of the elongate, flexible member 86. A nipple connector 119 may be provided on retainer socket member 100, as shown in FIG. 5; or the last connector 81 at the first end 87 of flexible, elongate member 86, which is received by retainer socket member 100, may alternatively be provided with a nipple connector 119 (as shown in dotted lines), whereby fluid passageway 112 is in a fluid and gas transmitting relationship with fluid absorbent material 115 via tubular member 118. Thus, upon application of a suitable vacuum, or suction force, from suction pump 117, undesired fluids which have been assorbed by fluid absorbent material 115 are drawn, or sucked into tubular member 118, and in turn into passageway 112. In the embodiment shown in FIG. 6, tubular conduit 113 which is disposed in passageway 112 may be utilized in a similar manner to permit support arm 80 to be used in combination with a medical instrument 90 having fluid absorbent material 115 associated therewith. A nipple adaptor 119 (shown in dotted lines) is provided, which adaptor 119 is placed in a fluid transmitting relationship with tubular conduit 113.

With reference to FIGS. 1, 3, and 4, it is seen that support member 92, or skull clamp 108, has at least one passageway, or gas and fluid passageway, 120 and preferably a plurality of passageways 120 in fluid communication with a passageway 112 (or 113) of the elongate, flexible member 86. As shown at 117 in FIG. 1, at least one of the fluid passageways 120 is adapted for fluid communication with suction pump 117, in a manner which will be hereinafter described in greater detail. As seen in FIG. 1, there are a plurality of openings 104, adapted to receive the attachment means 91 of flexible support arm 80. If it is intended to utilize a suction device in connection with flexible arm 80, as previously described, the additional openings 104 in support member 92, or skull clamp 108, are sealed with a plurality of sealing plugs 121, which are inserted in any openings 104 which do not have a flexible arm associated therewith. Thus, upon operation of suction pump 117, and its being operatively associated with one of the passageways 120, a suction force can be transmitted through skull clamp 108 via passageway 120 and through the elongate flexible member 86 of flexible arm 80. As seen in FIG. 3, the plug members 121 have the same configuration as the attachment means 91 as previously described and like components bear like reference numerals. It should be noted that a plurality of flexible arms 80 can be supported by support member 92, or skull clamp 108.

Skull clamp 108 can be secured to a patient's skull (not shown) as by conventional skull screws 125 which pass through openings 126 in the lower base plate 127 of skull clamp 108, and are in turn screwed into a patient's skull (not shown) in a conventional manner. Skull clamp 108 may alternatively be positioned upon a suitable fixture disposed upon a patient's skull, or a fixture mounted adjacent the operating room table, whereby suitable posts (not shown) may be passed through openings 126 to secure skull clamp base member 127. Skull clamp base member 108 may further preferably include an intermediate plate member 128 and a top plate member 129, as shown in FIGS. 1 and 4. Plate members 127–129 may be fixedly secured to one another in any conventional manner into the configuration as shown in FIGS. 1 and 4; or alternatively, top plate 129 can be rotatably secured to intermediate plate member 128, whereby top plate member 129 can rotate about the longitudinal axis of intermediate plate member 128, in order to provide additional adjustability to skull clamp 108.

With reference to FIG. 6, it should be noted that tubular conduit 113 could also be representative of an electrical wire which can pass through the passageway 112 of elongate, flexible member 86, whereby support arm 80 of the present invention could be utilized to support an electrical, medical instrument 90; the electrical wiring therefore being provided through elongate, flexible member 86. The electrical wire, as represented by reference numeral 113 could pass outwardly of passageway 112 through nipple adaptor 119, or alternatively could pass directly through retainer means 89. At the second end 88 of elongate, flexible member 86, the electrical wire could pass through a passageway 120 in the support member 92, and hence to a desired electrical source in a conventional manner. Alternatively, electrical wire 113 could exit the elongate, flexible member 86 outwardly of attachment means 91, as by any suitable opening, whereby the wire would not pass through one of the passageways 120 and support member 92.

With respect to FIG. 7, an active medical instrument 90, such as a pair of scissor blades 130, may be disposed at the first end 87 of the elongate, flexible member 86, and support member 92 may be a pair of scissor handles 131. The desired force for closing the pair of scissor blades 130 can be provided by a cable 132 secured to one of the scissor blades 130, which cable in turn passes through passageway 112 of elongate, flexible member 86 and is operatively associated with one of the scissor handles 131. Accordingly, upon application of a suitable force, the elongate, flexible member 86 can be formed into any desired configuration to permit the medical instrument 90 to be supported at the desired location within the human body (not shown). It should be further noted that medical instrument 90 could be any other conventional type of medical instrument, such as a clip applier, fluid sucker, or needle holder.

With reference to FIG. 6, it is seen that passageway 112 may also be partially filled with a heat sensitive material 140 which may be disposed within passageway 112, or within a tubular conduit 113 disposed within passageway 112. Preferably, heat sensitive material 140 could be a plurality of polystyrene balls 141. After forming, or forcing, support arm 80 into a desired configuration, at a first temperature, which is desired to be permanently retained, support arm 80, having heat sensitive material 140 therein, may be heated to a second temperature which causes the heat sensitive material 140 to solidify and in turn permanently restrain movement of the plurality of connectors 81 which form elongate, flexible member 86.

It is to be understood that the invention is not limited to the exact details of construction, operation, exact materials, or embodiments shown and described, as obvious modifications and equivalents will be apparent to one skilled in the art; for example, the attachment means could be a threaded member which is threadedly received within the support member, as by rotating and screwing support arm into the support member. Accordingly, the invention is therefore to be limited only be the scope of the appended claims.

I claim:

1. A flexible, radiolucent support arm for medical instruments for use in surgical procedures comprising:

a plurality of plastic connectors, each connector having a first and second end, a ball member being disposed on the first end, and a socket member being disposed on the second end; the ball member of each connector being frictionally received within the socket member of an adjacent connector and retained in a desired geometric relationship with respect to an adjacent connector until a force sufficient to overcome the frictional force between the mating ball and socket member is applied to alter the orientation between adjacent connectors; the plurality of connectors being associated with each other to form an elongate, flexible member having first and second ends;

means for retaining a medical instrument disposed at the first end of the elongate, flexible member; and means for attaching the elongate, flexible member to a support member, the attachment means being disposed at the second end of the elongate, flexible member whereby upon application of a force, to at least some of the connectors, sufficient, to overcome the frictional force between adjacent connectors, the orientation of the first end of the elongate flexible member with respect to the second end of the elongate, flexible member may be altered into a second orientation which automatically remains until another force is applied to the elongate, flexible member.

2. The flexible, radiolucent support arm of claim 1, wherein the medical instrument is a brain retractor blade and the support member is a skull clamp.

3. The flexible, radiolucent support of claim 1, wherein the medical instrument has associated therewith a fluid absorbent material, and the elongate, flexible member includes means for applying a fluid suction force to the fluid absorbent material.

4. The flexible, radiolucent support arm of claim 3, wherein the fluid suction force application means includes a fluid passageway extending through the elongate, flexible member in fluid communication with the fluid absorbent material, and adapted to be associated with a suction pump.

5. The flexible, radiolucent support arm of claim 4, wherein a tubular member is disposed in fluid communication between the fluid absorbent material and the fluid passageway of the elongate, flexible member.

6. The flexible, radiolucent support arm of claim 4, wherein the fluid passageway of the elongate, flexible member is in fluid communication with at least one fluid passageway associated with the support member.

7. The flexible, radiolucent support arm of claim 6, wherein the support member is a skull clamp and the at least one fluid passageway of the skull clamp is adapted for fluid communication with a suction pump.

8. The flexible, radiolucent support arm of claim 1, wherein the medical instrument is a pair of scissor blades, and the support member is a pair of scissor handles.

9. THe flexible, radiolucent support arm of claim 1, wherein a passageway extends between the first and second ends of each connector, and each ball member is received within an adjacent socket member in a fluid and gas tight relationship, whereby a fluid and gas tight passageway extends between the first and second ends of the elongate, flexible member.

10. The flexible, radiolucent support arm of claim 1, wherein a passageway extends between the first and second ends of each connector to form a passageway extending between the first and second ends of the elongate, flexible member, and a fluid and gas tight, flexible conduit member is disposed within the passageway extending between the first and second ends of the flexible elongate member.

11. The flexible, radiolucent support arm of claim 1, wherein a passageway extends between the first and second ends of the flexible, elongate member, and an electrical wire extends therethrough in an electricity transmitting relationship between an electrical, medical instrument, adapted to be retained by the retaining means, and the support member.

12. The flexible, radiolucent support arm of claim 1, wherein a passageway extends between the first and second ends of the flexible, elongate member, and the passageway is at least partially filled with a heat sensitive material which first permits relative movement between adjacent connectors at a first temperature, and upon being heated to a second temperature subsequently does not permit relative movement between adjacent connectors.

13. The flexible, radiolucent support arm of claim 12, wherein the heat sensitive material is a plurality of polystyrene beads, which after being heated to the second temperature solidify to provide rigidity between adjacent connectors.

14. The flexible, radiolucent support arm of claim 2, wherein the skull clamp includes means for mounting the skull clamp to the skull of a patient.

15. The flexible, radiolucent support arm of claim 3, wherein the medical instrument is a brain retractor blade.

16. The flexible, radiolucent support arm of claim 1, wherein the medical instrument is a sucker, and the elongate, flexible member includes means for applying a fluid suction force to the fluid absorbent material.

* * * * *